(12) United States Patent
Harris

(10) Patent No.: US 12,702,753 B2
(45) Date of Patent: Aug. 11, 2026

(54) MECHANICALLY WOUND INFUSION PUMP

(71) Applicant: John David Harris, Encinitas, CA (US)

(72) Inventor: John David Harris, Encinitas, CA (US)

( * ) Notice: Subject to any disclaimer, the term of this patent is extended or adjusted under 35 U.S.C. 154(b) by 1323 days.

(21) Appl. No.: 17/460,111

(22) Filed: Aug. 27, 2021

(65) Prior Publication Data

US 2022/0062531 A1 Mar. 3, 2022

Related U.S. Application Data

(60) Provisional application No. 63/072,026, filed on Aug. 28, 2020.

(51) Int. Cl.
*A61M 5/145* (2006.01)
*A61M 5/168* (2006.01)

(52) U.S. Cl.
CPC ........ *A61M 5/145* (2013.01); *A61M 5/16877* (2013.01); *A61M 2005/14506* (2013.01)

(58) Field of Classification Search
CPC .............. A61M 5/145; A61M 5/16877; A61M 2005/14506
See application file for complete search history.

(56) References Cited

U.S. PATENT DOCUMENTS 6,267,559 B1 * 7/2001 Mossman ............ F04B 43/082 417/44.1
2018/0304029 A1 * 10/2018 Koch ................. A61M 5/1454

OTHER PUBLICATIONS

The Power-Reserve Indicator from A. Lange & Sohne https://www.youtube.com/watch?v=1hM1aASc8qw as early as Aug. 18, 2020.

* cited by examiner

*Primary Examiner* — Dung T Ulsh
(74) *Attorney, Agent, or Firm* — Clayton Howarth, P.C.

(57) ABSTRACT

This disclosure relates generally to an apparatus for creating a mechanically-wound infusion pump which can be used in a medical context to provide steady, reliable mechanical infusion amounts without relying on electricity and which can operate accurately in areas where electric power is not available or when ambulation is desired.

15 Claims, 6 Drawing Sheets

MECHANICALLY WOUND INFUSION PUMP

CROSS-REFERENCE TO RELATED APPLICATIONS

This application claims the benefit of U.S. Provisional Patent Application Ser. No. 63/072,026, filed Aug. 28, 2020, which is hereby incorporated by reference herein in its entirety including, but not limited to those portions that specifically appear hereinafter, the incorporation by reference being made with the following exception: In the event that any portion of the above-referenced application is inconsistent with this application, this application supercedes the above-referenced application.

STATEMENT REGARDING FEDERALLY SPONSORED RESEARCH AND DEVELOPMENT

Not Applicable.

BACKGROUND

This disclosure is particularly directed towards a mechanically wound infusion pump which operates to regulate and pump infusions of fluid through the use of a mechanically wound pump rather than an electrically powered or elastomeric pump. In addition to a mechanically wound infusion pump, the disclosure is directed to a mechanically wound pump used for moving fluids from one location to another.

An external infusion pump is used in a medical context to deliver needed fluids to a patient in a controlled manner. These devices can be used to deliver nutrients, medications, or a wide variety of other medical fluids in a medical setting. These pumps can be designed for specific purposes, but the most common methods involve powering the pumps by electricity. Electric pumps have a wide variety of features that allow the fluid to be delivered in precise increments and in precise intervals, but suffer from the problem of requiring electricity to operate. In situations where electricity is not available, a variety of methods have developed, most of which require relying on fluid pressure to supply desired medical fluids. These systems require a great deal of specialized knowledge on the part of those operating them and do not allow for the precise control of electrical pumps. There have been battery powered electric pumps, specifically designed for times when ambulation is desired, but such pumps require either regular access to new batteries or to an electric power source to re-charge batteries.

While there is little that can match the precision of a digital controller with suitable feedback, for centuries mechanical watch makers have created devices which provide precision measurement with only mechanical apparatus. A modern mechanical watch can keep accurate time within seconds per day, or better. However, up to this point, non-electrical provision of medical fluids has not leveraged this precision. What is needed is an apparatus which can take advantage of the lessons learned in creating precise mechanical timekeeping instruments and create a precise mechanical pump for medical infusions when electricity is unavailable or unreliable. Such a device could be used as an emergency backup in a modern hospital setting, or for general treatment in a wide variety of situations where electricity may not be available or when ambulation is desired.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein. It should be noted that while the preferred illustrated embodiment of this disclosure is used as a precision medical device, the disclosed invention can be adapted for use in any situation where precision pumping of fluids is required or desired without the use of electricity. For example, the present disclosure can be adapted to pumping fluid from one container to another, as a siphon.

SUMMARY OF THE DISCLOSURE

The purpose of the instant disclosure is to create a mechanically wound infusion pump which uses precise mechanical components to provide precision dosing of medical or other fluids. The illustrative apparatus uses a mechanical system based on a mainspring and a series of gears which turns the main infusion wheel, combined with an escapement which allows the main infusion wheel to turn at a precise rate and causes the pump to operate at a precise rate. The main infusion wheel can operate as a peristaltic pump, being in direct contact with a length of flexible tubing, or it can be modified to operate another type of pump.

DETAILED DESCRIPTION

For the purposes of promoting an understanding of the principles in accordance with this disclosure, reference will now be made to illustrative embodiments of the invention. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, processes and methods will be disclosed and described, it is to be understood that this disclosure is not limited to the particular configurations, process steps, and materials disclosed herein, as such configurations, process steps, and materials may vary somewhat. It is also to be understood that the terminology employed herein is used for the purpose of describing particular illustrative embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a", "an", and "the" include plural referents unless the context clearly dictates otherwise.

As used herein, the terms "comprising," "including," "containing," "characterized by," "having" and grammatical equivalents thereof are inclusive or open-ended terms that do not exclude additional, unrecited elements or method steps.

Figure 1:
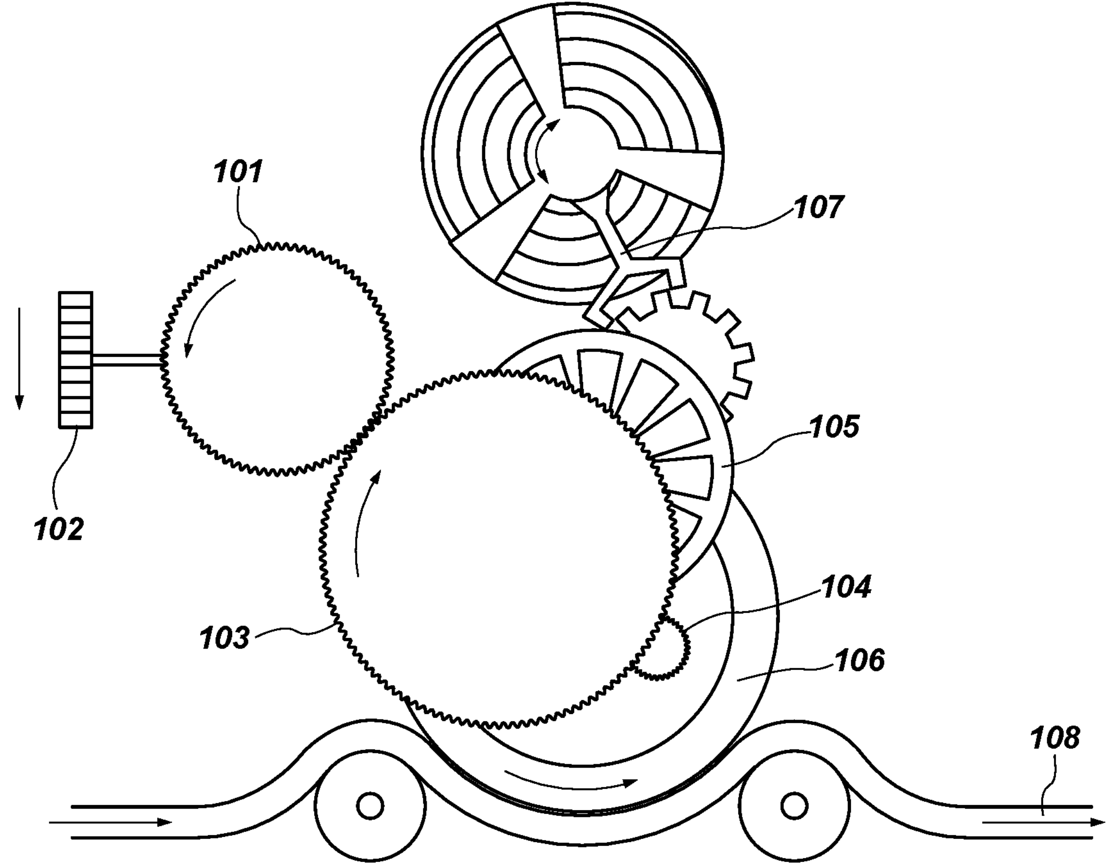
FIG. 1 is an overview showing the interior workings of one embodiment of the apparatus.

FIG. 1 shows the interior elements of a mechanically wound infusion pump. A winding gear 101 is attached to a crown 102 which protrudes from a housing. The crown is twisted and turns the winding gear 101, which stores energy in the mechanical power reserve 103. In one embodiment, the mechanical power reserve 103 is a mainspring assembly. In one embodiment, turning the mainspring assembly of the mechanical power reserve 103 winds the mainspring and stores energy within the mainspring. In one embodiment the mainspring assembly 103 comprises a method for storing mechanical energy. In one embodiment the mainspring assembly comprises a mainspring, a barrel, and a gear. In one embodiment, the mainspring may comprise a coiled spring within the barrel, which stores energy as it is wound. One embodiment of the mainspring may be a thin strip of metal wound upon itself multiple times. This mainspring may be contained in a cylindrical barrel, which is connected to a gear. In one embodiment, the gear may comprise one exterior face of the cylindrical barrel. The mainspring assembly may also comprise a winding pinion located within the cylindrical barrel. The strip of metal comprising the mainspring may be connected to the barrel at one end and to the winding pinion at the other end. In one embodiment, the winding pinion may additionally be connected to the winding gear 101. In another embodiment, the winding pinion may be secured in place, while the winding gear is connected to the gear of the mainspring assembly. This causes the mainspring itself to be wound and store energy as the mainspring assembly 103 is rotated by the winding gear 101. In another embodiment, other means for storing energy in the mechanical power reserve are possible. For example, an automatic winding mechanism which uses movement to wind a mainspring could be used. Furthermore, other types of mechanical power supply may use different means for storing energy in the mechanical power reserve.

The mechanical power reserve 103 may have a click assembly 104 attached to the barrel which allows the mainspring assembly to turn in only one direction. The click assembly 104 may be a simple lever attached to a pivot with a sloped edge which fits into the teeth of the mainspring assembly and allows the assembly to rotate in one direction (when being wound), but catches in the teeth of the mainspring assembly preventing the assembly from slipping in the opposite direction. The click assembly may also be in any other form which will allow the mainspring assembly to turn in only one direction. This causes energy in the mainspring to be released only through the wheel train 105, which is precisely regulated by the escapement 107. In one embodiment, the wheel train 105 is comprised of a series of gears which are turned by the mechanical power reserve 103, and which are regulated by the escapement 107. In one embodiment the wheel train 105 is used to transfer energy from the mechanical power 103 reserve to the main infusion wheel 106. This transfer of energy is regulated by the escapement 107.

Figure 7:
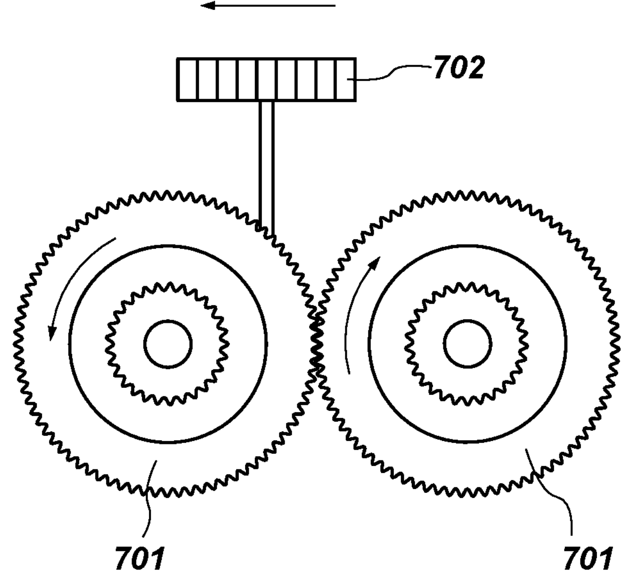
FIG. 7 shows an example of an apparatus with two mainspring assemblies used as the mechanical power supply.

In one embodiment the mainspring may be comprised of a larger strip of metal, or may be made from another material suitable for storing energy in a similar manner. In yet another embodiment, shown in FIG. 7, the single mainspring assembly in the mechanical power reserve is replaced by two or more mainspring assemblies 701 which are connected to each other and to the winding crown 702 to allow for more energy to be stored in the mechanical power reserve. FIG. 7 shows only the mechanical power reserve and winding crown which is located in the same location as shown in FIG. 1 and those skilled in the art will appreciate implementing the embodiment in FIG. 7. In another embodiment, a different type of mechanical power reserve may be provided. For example, the main power reserve may store energy in any other appropriate manner which allows energy to be transferred to the pump.

Referring to FIG. 1, with the click assembly 104 preventing the backward release of energy, energy stored in the mainspring is released only through the wheel train 105. The wheel train 105 is driven by the mainspring assembly 103 and drives the main infusion wheel 106. The wheel train is also connected to the escapement 107, which allows for the precise regulation of the rate at which the wheel train 105 turns. The wheel train 105 in turn drives the main infusion wheel 106, and so the combination of the operation of the escapement 107, the size and arrangement of gears in the wheel train 105, and the size of the main infusion wheel 106 determines the pumping rate. This rate is kept steady by the operation of the escapement 107, and the gear train 105 and main infusion wheel 106 may be manufactured with a variety of specific measurements to produce a variety of pumping rates as may be needed for a variety of infusions, which in one embodiment are pumped through a length of flexible tubing 108 by the main infusion wheel 106.

Figure 2:
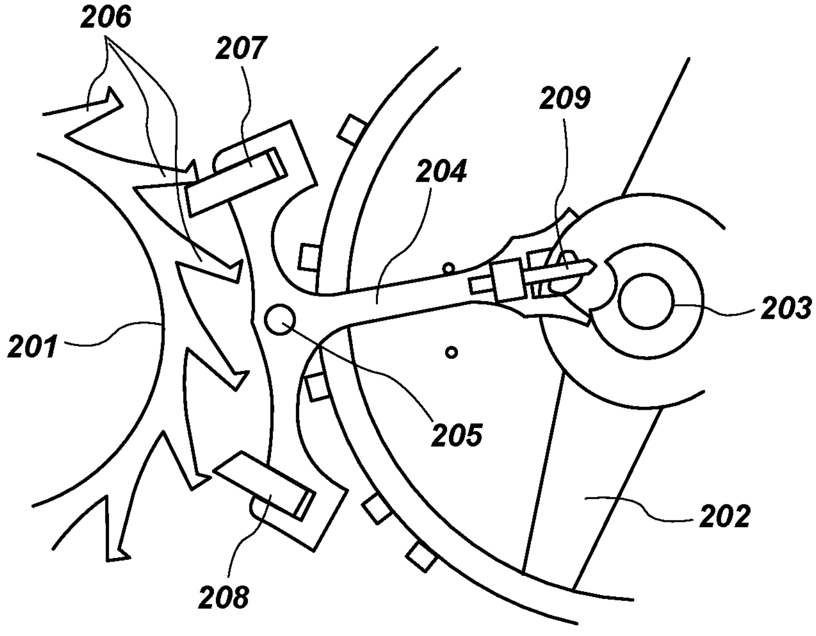
FIG. 2 is a diagram showing one embodiment of the escapement of the apparatus.

FIG. 2 shows one illustrative embodiment of the escapement 107. This embodiment shows an escapement patterned after a classical lever escapement used in a mechanical watch, but any type of mechanism which regulates the release of mechanical energy from the mechanical power reserve would be within the current disclosure. The escapement allows energy from the mechanical power reserve to be released in regular increments rather than all at once. In the illustrated embodiment, the escapement comprises an escape wheel 201, a balance wheel 202 including a hairspring 203, and a pallet fork 204 attached to a pivot 205. The escape wheel 201 is connected to the wheel train 105 and must rotate for the wheel assembly to turn and release energy. As seen in FIG. 2, the escape wheel 201 comprises a gear with a series of teeth 206 that are angled from perpendicular to the circumference of the circle. The pallet fork 204 is a forked lever which can rotate across its pivot 205 and which has two prongs 207-208 which engage with the teeth 206 of the escape wheel 201. The opposite end of the pallet fork has a pin 209 which engages with the balance wheel 202. The prongs 207-208 are designed to alternately engage the escape wheel as it rotates back and forth. Meanwhile, the end pin 209 engages with the balance wheel 202 and rotates the balance wheel 202 when the pallet fork 204 pivots. The balance wheel is also attached to the hairspring 203, which is wound around the balance wheel 202. The hairspring 203 is put under pressure when the balance wheel 202 rotates and exerts a force to return the balance wheel to a neutral position, which also pushes on the pin 209 of the pallet fork, 204, causing it to rotate about the pivot 205.

As energy from the mainspring (transferred through the gear train) causes the escape wheel 201 to rotate, the escape wheel engages the first prong 207 of the pallet fork and pushes it down causing the pallet fork 204 to rotate about the pivot 205. As the pallet fork pivots, the pin 209 rotates the balance wheel causing the hairspring 203 to be wound, exerting a force to return the balance wheel 203 (and pallet fork 204) to a neutral position. Likewise, as the pallet fork 204 pivots, the second prong 208 engages the escape wheel 201, causing it to stop moving. At this point, the pressure exerted by the hairspring 203 causes the balance wheel 202 to rotate the opposite direction as before, pushing the end pin 209 of the pallet fork 204 and causing it to rotate in the opposite direction, disengaging the second prong 208 of the pallet fork from the escape wheel 201 and allowing it to rotate, which again engages the first prong 207 of the pallet fork 204, again causing it to pivot and engage the second fork 208, stopping the escape wheel. The back and forth motion powered by the hairspring 203 and energy from the mainspring is what regulates the release of energy from the mainspring through the wheel assembly and main infusion wheel, regulating the speed of the pump. In one embodiment, the active length of the hairspring may be adjustable.

In one illustrative embodiment, referring again to FIG. 1, the operation of the escapement, 107 represented in FIG. 2, regulates the speed of the wheel train 105 and the release of energy from the mainspring assembly 103 into the wheel train 105, regulating the speed of the main infusion wheel 106 and the rate of flow from the pump. The wheel train 105 and the precise combination of gears used can also affect the speed of the main infusion wheel and thus the speed of the pump. In one illustrative embodiment, it will be appreciated that different apparatus can be constructed to have different pumping rates for different types of infusion or other different uses. In another illustrative embodiment, the precise speed of the release of energy is regulated by the hairspring 203. In yet another illustrative embodiment, the release of energy can be adjusted by adjusting the hairspring. In a still further illustrative embodiment, the hairspring has a number of regulator pins which can be moved to alter the active length of the hairspring, thus altering the energy stored in the hairspring with each motion of the pallet fork and the length of time of each motion of the pallet fork. The regulator pins may contact different parts of the hairspring, causing only a portion of the length of the hairspring to be active in returning the balance wheel to a neutral position. This alters the amount of energy stored in the hairspring in each movement of the balance wheel, and changes the rotation rate of the escape wheel and of the wheel train and main infusion wheel. In one embodiment, the active length of the hairspring may be adjustable through a dial or control on the housing, which may move the regulator pins. In another embodiment, a dial on the housing may adjust the energy stored in the hairspring with each movement of the balance wheel in another manner.

In another illustrative embodiment, it will be appreciated that other means may be used to adjust the speed of the main infusion wheel, such as using different gears to adjust the speed at which the main infusion wheel rotates. A lever may be used to slide additional gears or different gears into the wheel train, thus changing the speed of the main infusion wheel.

Figure 3:
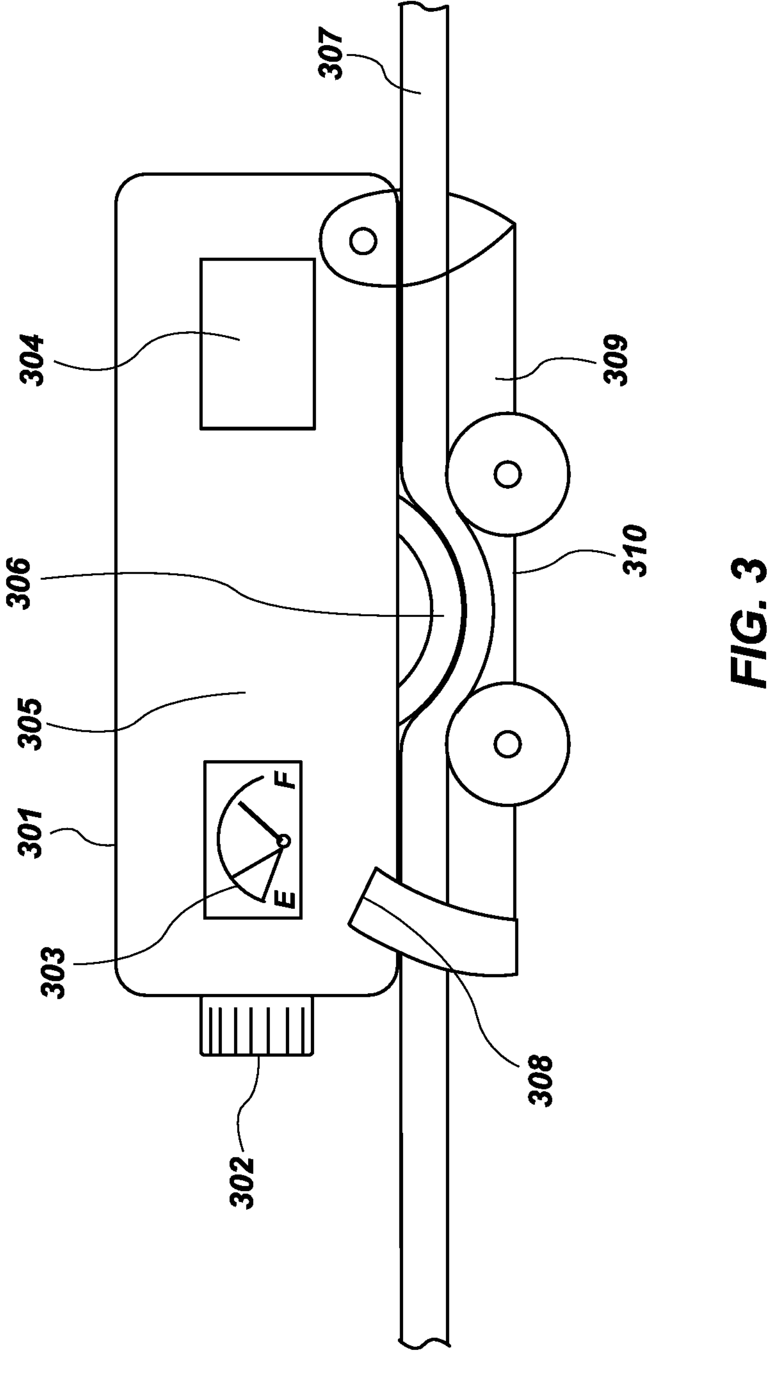
FIG. 3 is a diagram showing the exterior of one embodiment of the apparatus, showing one method of connecting flexible tubing to the apparatus.

One illustrative embodiment of the exterior of the apparatus is shown in FIG. 3. In one embodiment of the apparatus in FIG. 3 a housing 301 encloses the mechanical parts of the apparatus forming the movement portion 305 (not explicitly shown) of the apparatus. The movement 305 also includes the winding crown 302 (102 in FIG. 1), which is twisted to add power to the mechanical power reserve and operate the mechanical portion of the device. Additionally, a power reserve indicator 303 and a window 304 which shows the operation of the mechanism may be present. The movement includes the wheel train, which turns the main infusion wheel 306 (106 in FIG. 1). In one embodiment the main infusion wheel is used to power a pump.

Still referring to FIG. 3, in one illustrative embodiment the main infusion wheel 306 operates as the pump. In said embodiment the main infusion wheel 306 protrudes from the housing 301. The main infusion wheel 306 protrudes from the housing 301 in a location where flexible tubing 307 is attached tightly to the housing 301 by the use of a snap lock mechanism 308. The mechanism secures the tubing 307 to the pump housing 301 with a backing on the opposite side 309. The tubing 307 is secured tightly enough that it can be compressed (where the tubing is closed off by pressure from the main infusion wheel) or relaxed (where the tubing is in an open position). In one embodiment the main infusion wheel 306 has at least one raised portion which is brought into contact with different sections of the flexible tubing 307 as the wheel rotates. When the raised portion is brought into contact with the flexible tubing 307, the tubing is compressed and closed off. As the raised portion of the main infusion wheel 306 rotates, the tubing is released and allowed to open. As the tubing 307 is compressed and released in different areas where it contacts the main infusion wheel 306, it causes the fluid to be pumped through the tubing 307 by a peristaltic pumping effect.

In one illustrative embodiment, the tubing 307 and the backing 309 are part of a disposable set which is specifically designed for a particular infusion, this being the infusion set 310. For example, one set may be designed for a saline infusion while another is designed for small amounts of a medication such as opioids or other small dose medication. Each set may use a particular tubing size to create a different flow rate for a particular infusion, and may be connected to a different size reservoir. Continuing to refer to FIG. 3, alternatively, the various parts of each set may be interchangeable to create an appropriate infusion set 310 for a particular fluid and a particular patient. Additionally, the movement 305 may be manufactured with different wheel trains or power reserves, or with different hairspring adjustments to adjust the rate at which the main infusion wheel 306 turns, thus creating a different flow rate or different length of infusion. The different movements 305 may be color coded to indicate the differences.

In one illustrative embodiment, a hacking lever is installed as part of the movement, so as to stop the motion of the mechanism when engaged. This lever may operate by pushing against the balance wheel when engaged, thus stopping its motion and stopping the turning of the gears. Alternatively, it may operate in any other method which stops the motion of the mechanism. The hacking lever may be attached to the main infusion wheel 306 such that when the tubing is removed the hacking lever engages, stopping the motion of the apparatus. Alternatively, the hacking lever may be attached to the winding crown so that when it is pulled out the motion stops as is known in the art of mechanical watches. Additionally, and alternatively, the lever may be attached to a separate knob or button which protrudes from the housing, such that when it is operated, the motion of the mechanism stops, thus stopping the pumping of the fluid.

In another illustrative embodiment, the main infusion wheel can be used to power other types of pumps to move fluid. For example, the main infusion wheel may be attached to a series of gears which are used to power a peristaltic pump which operates by pinching off sections of a tube in a linear sequence. These gears may translate the rotational motion of the gears to a linear motion of a series of teeth through the use of cams, and the teeth may compress sections of flexible tubing in a linear sequence. Additionally, the energy released through the main infusion wheel may be transformed through the use of appropriate gears or other mechanical transformers to power a number of different types of mechanical pump used to transfer fluid from one location to another.

In the illustrative embodiments of the present disclosure, the entire apparatus may be constructed of appropriate, sanitary, medical compatible material, and be designed as a single-use device.

Figure 4A:
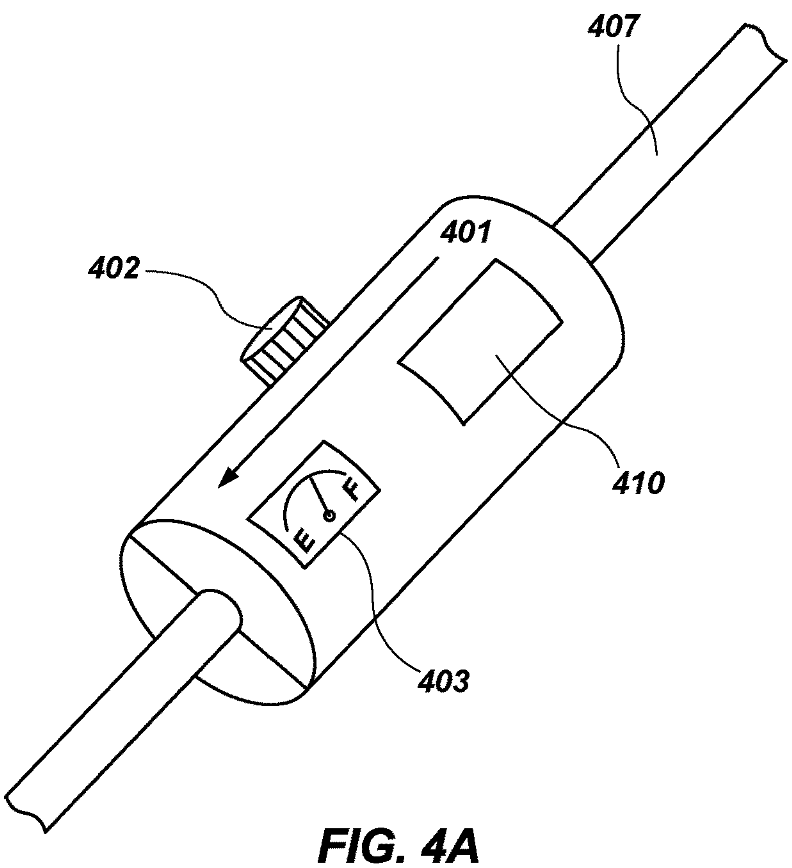
FIGS. 4A-4B show the exterior of another embodiment of the apparatus, with FIG. 4A showing the apparatus closed with flexible tubing and FIG. 4B showing the apparatus open showing where the flexible tubing fits.
Figure 4B:
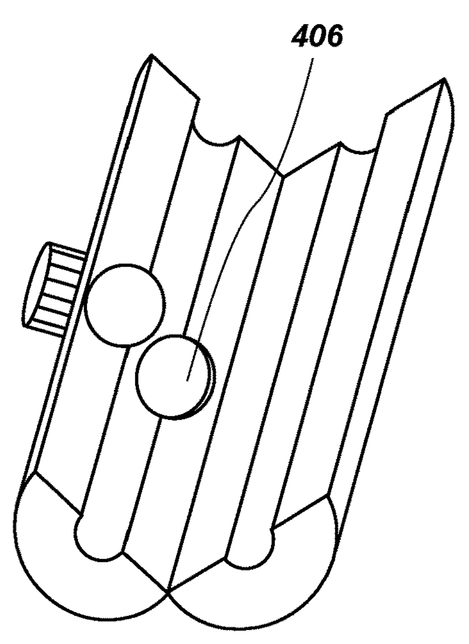

FIGS. 4A-4B show another illustrative embodiment of the apparatus, representing a different housing arrangement. FIG. 4A shows the housing 401 closed around the flexible tubing 407 while FIG. 4B shows the housing 401 open showing the internal location of the tubing 407 as related to the internal working parts, including the main infusion wheel 406. The arrow in FIG. 4A indicates the direction of travel of the fluid in one embodiment. The housing 401 may be hinged, or it may be connected on top and bottom through other means that secure it in place around the flexible tubing 407. The apparatus can be placed around the flexible tubing 407 in such a way that the main infusion wheel 406 comes into contact with the flexible tubing 407 and allows the fluid in the tubing to be pumped through a peristaltic operation, similar to the method of pumping in previous illustrative embodiments. The housing 401 contains a winding crown 402 and power reserve indicator 403. In addition, controls for adjusting the flow rate 410 may be present on the housing. These controls may adjust the active length of the hairspring or may control the speed of the main infusion wheel in a different manner.

In one illustrative embodiment, the mechanism may be designed with an automatic winding feature for an ambulatory pump, by way of illustration and not limitation, such as an insulin pump. That is, the mechanism is equipped with a device which translates the motion of the pump as the body moves into energy which adds to the mechanical power reserve. In one illustrative embodiment, where the mechanical power reserve is a mainspring, this automatic winding mechanism may comprise an oscillating weight attached to a pivot. As the user's body moves, the motions cause the oscillating weight to pivot and move a rotor, which is attached to a ratcheted winding mechanism. This ratcheted winding mechanism may be connected to a number of gears, allowing it to wind the mainspring using the motion of the user's body. The precise form of the automatic winding mechanism may vary depending on where on the body it would be worn, as daily tasks involve different parts of the body moving in different ways. One illustrative embodiment of the invention has both an automatic winding mechanism and a winding wheel and crown mechanism so that in addition to automatically winding the mainspring, power may be added to the mechanical power reserve manually as well.

In one illustrative embodiment of the apparatus, referring now to FIG. 3, a power reserve indicator 303 is present on the exterior of the housing. This indicator 303 is connected to the mechanical power reserve 103 and indicates the remaining power in the reserve, thus allowing a user to easily see when the mechanical power reserve needs to be wound. In one illustrative embodiment this indicator is a mechanical indicator which is connected to the mechanical power reserve through one or more gears. When the device is wound, the power reserve indicator moves to show the extent of the power stored in the mechanical power reserve. As energy is released from the mechanical power reserve, it causes the power reserve indicator to move indicating that less power is available in the mechanical power reserve. The indicator may be a needle which indicates linearly across a region how much power remains, or it may be a needle which rotates, or any other type of indicator which moves as power in the mechanical power reserve decreases. The indicating device itself may have indications in time, such as "6 hours, 4 hours, 2 hours," which are placed so the needle reaches each point when the mechanical power reserve has power for that much time of operation remaining, or it may simply indicate a level of power between the maximum and no energy, e.g., "Full" and "Empty" with marks in between.

Figure 5:
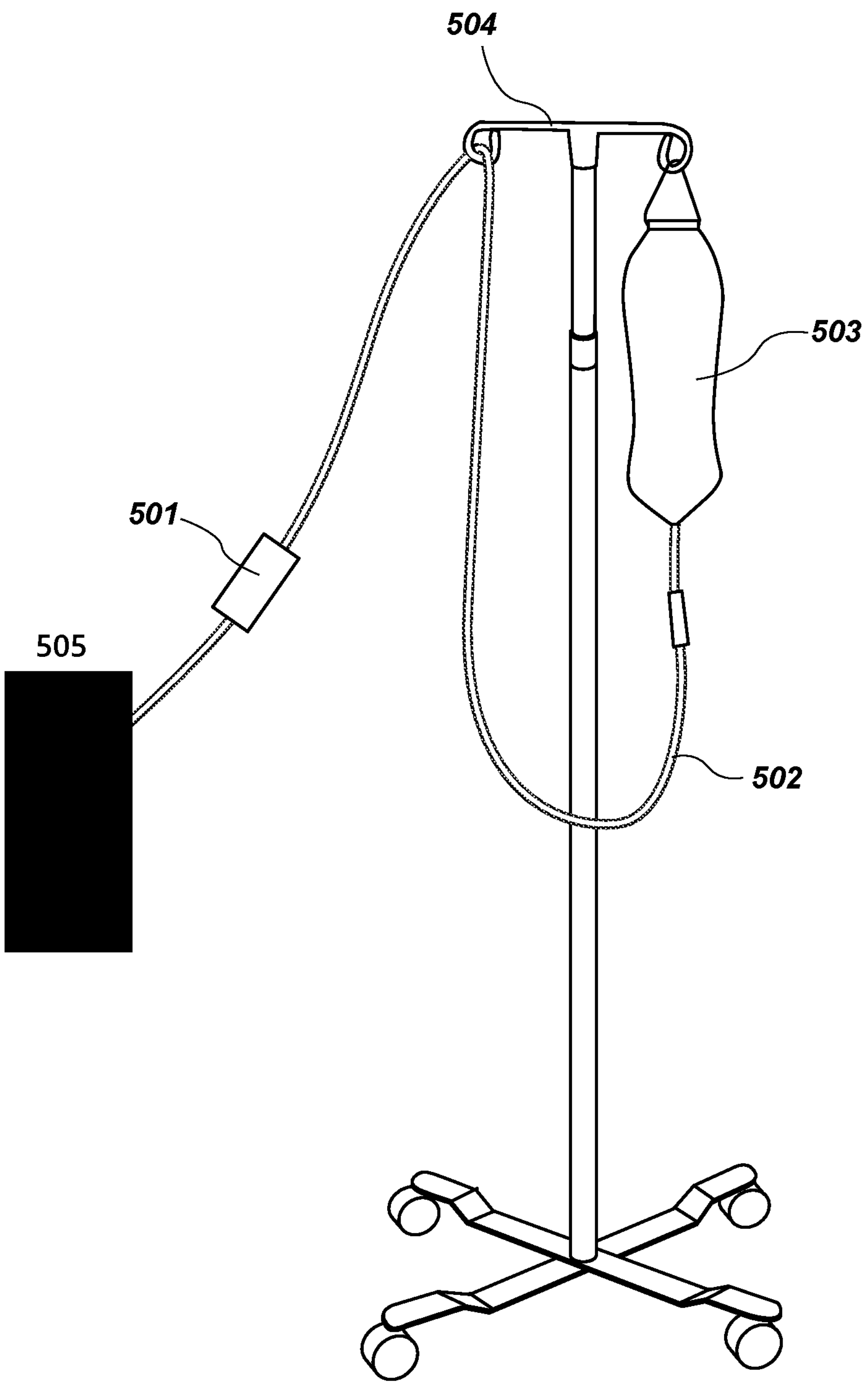
FIG. 5 shows the location of the apparatus on flexible tubing between an W reservoir and a patient.
Figure 6:
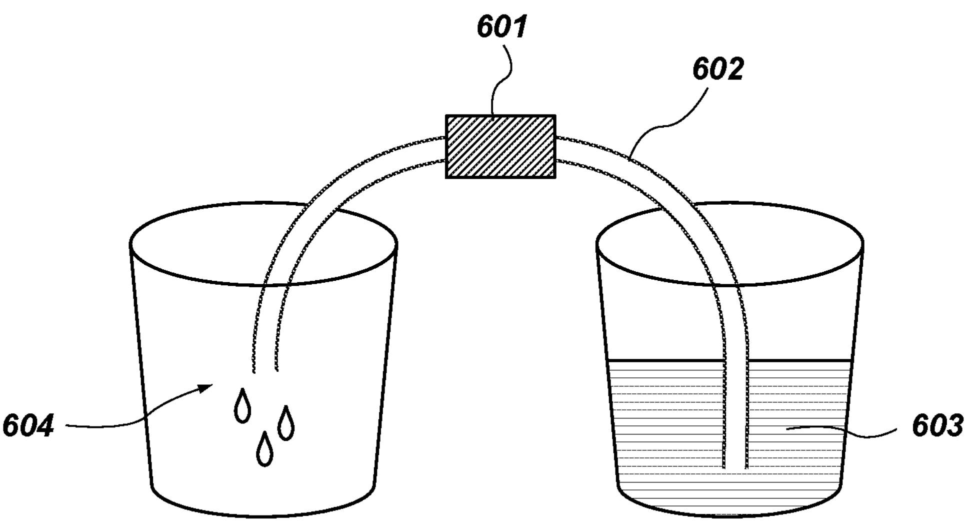
FIG. 6 shows the apparatus located on flexible tubing between a reservoir and another container of fluid, being used to move fluid from one location to another.

As shown in FIG. 5, the illustrative apparatus 501 may be connected to flexible tubing 502 that runs between an intravenous (IV) reservoir 503 and a patient 505. The IV reservoir may be hung from a pole 504 in one illustrative embodiment, or it may be worn by a patient. FIG. 6 shows another illustrative embodiment wherein the apparatus 601 is used to move fluid through a flexible tubing 602 from one reservoir 603 to another reservoir 604. While specific types of reservoir are shown, it will be appreciated that the apparatus may be used to move liquid between any number of types of reservoir.

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of any single foregoing disclosed illustrative embodiment. Thus, the following claims are hereby incorporated into this Detailed Description by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in quantities, proportions, materials, and manner of making and use may be made without departing from the principles and concepts set forth herein. In particular, by way of example and not limitation, while the primary motivation is for use as a medical infusion pump, it will be apparent to those of ordinary skill in the art that the disclosed invention may be used as a precision pump for any number of fluids, not only as a medical infusion pump.

What is claimed is:

1. An apparatus for a mechanical pump, comprising:

a mechanical power reserve;

a wheel train, wherein the wheel train comprises a series of gears and wheels through which an energy from the mechanical power reserve is transferred to a main infusion wheel;

an escapement comprising an escape wheel, a balance wheel, a pallet fork, and a hairspring, wherein the escape wheel is attached to the wheel train, and wherein the hairspring is attached to the balance wheel to allow the balance wheel to swing in precise increments, and wherein the balance wheel is connected to the pallet fork which causes the pallet fork to move back and forth in precise increments, which in turn causes the escape wheel and the wheel train to move in precise increments; and, the main infusion wheel which powers the mechanical pump, wherein the main infusion wheel is turned by the wheel train.

2. The apparatus of claim 1, also comprising means for storing the energy in the mechanical power reserve.

3. The apparatus of claim 1 also comprising a means for adjusting an amount of the hairspring which is active, thus adjusting a rate at which the balance wheel turns, changing a rate at which the escape wheel and the wheel train turn, thereby adjusting a speed of the mechanical pump.

4. The apparatus of claim 3 wherein the means for adjusting the amount of the hairspring which is active comprises one or more movable regulator pins which can be adjusted to alter an active length of the hairspring.

5. The apparatus of claim 1 wherein the mechanical pump comprises a linear peristaltic pump, wherein the mechanical power reserve turns the series of gears that operate a series of compression elements, causing said elements to compress and relax a length of a flexible tubing in sequence, thereby pumping fluid through the flexible tubing.

6. The apparatus of claim 1 wherein the mechanical power reserve comprises at least one mainspring, barrel and gear forming a mainspring assembly.

7. An apparatus for a mechanically wound infusion pump, comprising:

a housing;

a winding crown;

a mechanical power reserve, connected to the winding crown such that when the winding crown is twisted, power is stored in the mechanical power reserve;

a wheel train by which power is transferred from the mechanical power reserve to a main infusion wheel;

the main infusion wheel which powers the mechanically wound infusion pump; and, an escapement comprising an escape wheel, a balance wheel, a pallet fork, and a hairspring, wherein the escape wheel is attached to the wheel train, and wherein the hairspring is attached to the balance wheel to allow the balance wheel to swing in precise increments, and wherein the balance wheel is connected to the pallet fork which causes the pallet fork to move back and forth in precise increments, which in turn causes the escape wheel, the wheel train, and the main infusion wheel to move in precise increments, which allows for precise determination of the amount of fluid to be pumped, controlled by a rate of rotation of the main infusion wheel.

8. The apparatus of claim 7, wherein the mechanical power reserve comprises at least one mainspring, barrel and gear forming a mainspring assembly, the mainspring assembly being connected to the winding crown and the wheel train.

9. An apparatus for a mechanically wound infusion pump, comprising a housing;

a winding crown;

a mechanical power reserve connected to the winding crown;

a wheel train connected to the mechanical power reserve by which a power is transferred from the mechanical power reserve to a main infusion wheel;

an escapement which regulates a release of energy from the mechanical power reserve through the wheel train comprising an escape wheel, a balance wheel, a pallet fork, and a hairspring, wherein the escape wheel is attached to the wheel train, and wherein the hairspring is attached to the balance wheel to swing in precise increments, and wherein the balance wheel is connected to the pallet fork which causes the pallet fork to move back and forth in precise increments, which in turn regulates the release of energy from the mechanical power reserve through the wheel train;

the main infusion wheel; and, wherein the main infusion wheel is turned by the wheel train and powers the mechanically wound infusion pump.

10. The apparatus of claim 9, wherein the mechanical power reserve comprises at least one mainspring, barrel, and gear forming a mainspring assembly, the mainspring assembly being connected to the winding crown and the wheel train.

11. The apparatus of claim 9, wherein the mechanical power reserve comprises at least two or more mainspring assemblies connected to each other so as to store additional power in the mechanical power reserve, the mainspring assemblies being connected to the winding crown and the wheel train.

12. The apparatus of claim 9 wherein the wheel train comprises a series of gears turned by the main power reserve and regulated by the escapement.

13. A method of pumping fluid without using electricity comprising;

providing a mechanical power reserve;

providing a means for storing energy within the mechanical power reserve;

providing a pump;

regulating a release of energy from the mechanical power reserve through the use of an escapement;

transferring the energy from the mechanical power reserve through a series of gears to the pump; and, using the energy released from the mechanical power reserve to power the pump;

wherein the escapement comprises an escape wheel, a balance wheel, a pallet fork, and a hairspring, wherein the escape wheel is connected to the series of gears through which energy is transferred from the power reserve to the pump, and wherein the hairspring is attached to the balance wheel to allow the balance wheel to swing in precise increments, and wherein the balance wheel is connected to the pallet fork which causes the pallet fork to move back and forth in precise increments, which in turn causes the escape wheel to move in precise increments, thus regulating the energy transferred from the power reserve to the pump.

14. The method of claim 13 wherein the mechanical power reserve comprises at least one mainspring, barrel and gear forming a mainspring assembly.

15. The method of claim 14 also comprising turning a winding crown attached to the mainspring assembly in order to store energy in the mainspring assembly.

* * * * *